US012599691B2

(12) United States Patent (10) Patent No.: US 12,599,691 B2
Boukari (45) Date of Patent: Apr. 14, 2026

(54) METHOD AND DEVICE FOR DISINFECTING AND CLEANING ENCLOSED SPACES IN PARTICULAR, SUCH AS A PASSENGER COMPARTMENT ON A MEANS OF TRANSPORT

(71) Applicants: Morou Boukari, Toulouse (FR); PRODOSE, Bessieres (FR)

(72) Inventor: Morou Boukari, Toulouse (FR)

(73) Assignees: PRODOSE, Toulouse (FR); Morou Boukari, Toulouse (FR)

( * ) Notice: Subject to any disclaimer, the term of this patent is extended or adjusted under 35 U.S.C. 154(b) by 742 days.

(21) Appl. No.: 17/922,333

(22) PCT Filed: Apr. 28, 2021

(86) PCT No.: PCT/FR2021/000042
§ 371 (c)(1),
(2) Date: Mar. 13, 2023

(87) PCT Pub. No.: WO2021/219944
PCT Pub. Date: Nov. 4, 2021

(65) Prior Publication Data
US 2023/0211034 A1 Jul. 6, 2023

Related U.S. Application Data

(60) Provisional application No. 63/030,541, filed on May 27, 2020, provisional application No. 63/020,157, (Continued)

(51) Int. Cl.
*A61L 9/14* (2006.01)
*A61L 2/22* (2006.01)
(Continued)

(52) U.S. Cl.
CPC .................... *A61L 9/14* (2013.01); *A61L 2/22* (2013.01); *B01D 53/32* (2013.01); *B05B 7/045* (2013.01); (Continued)

(58) Field of Classification Search
CPC ....................................................... A61L 9/14
See application file for complete search history.

(56) References Cited

U.S. PATENT DOCUMENTS 4,546,923 A 10/1985 Ii
5,855,653 A 1/1999 Yamamoto
(Continued)

FOREIGN PATENT DOCUMENTS

| CA | 2 494 940 | 2/2004 |
| CN | 105841265 | 8/2016 |
| WO | 2010/140702 | 12/2010 |

OTHER PUBLICATIONS

Anonymous. "Disinfectant Spray—Lavender Scent I Seventh Generation" Feb. 26, 2019 (Feb. 26, 2019). pp. 1-8. Retrieved from the Internet: https://www.seventhgeneration.com/disinfectant-spray-lavender-vanilla-thyme-scent [retrieved on Aug. 23, 2021](Submission Pending).
(Continued)

*Primary Examiner* — Kevin Joyner
(74) *Attorney, Agent, or Firm* — NIXON & VANDERHYE

(57) ABSTRACT

Disclosed is a method for disinfecting and cleaning to prevent contamination of a passenger vehicle, characterized in that it includes the following operations:—installing at least one filter and condenser in the ventilation circuit; creating a swirling vortex of a disinfectant liquid by a gas referred to as a driving gas; spraying the swirling mixture created onto the clothing and luggage of passengers before they enter the passenger compartment; and spraying the
(Continued)

mixture created onto the solid surfaces and/or into the air of the passenger compartment to be disinfected. Also disclosed is a device for implementing the method.

12 Claims, 9 Drawing Sheets

Related U.S. Application Data filed on May 5, 2020, provisional application No. 63/016,660, filed on Apr. 28, 2020.

(51) Int. Cl.

| | |
|---|---|
| *B01D 53/32* | (2006.01) |
| *B05B 7/04* | (2006.01) |
| *B05B 7/10* | (2006.01) |
| *B64F 5/30* | (2017.01) |

(52) U.S. Cl.
CPC ................. *B05B 7/10* (2013.01); *B64F 5/30* (2017.01); *A61L 2202/15* (2013.01); *A61L 2202/25* (2013.01); *A61L 2209/14* (2013.01); *A61L 2209/16* (2013.01); *B01D 2257/106* (2013.01); *B01D 2257/91* (2013.01); *B01D 2258/06* (2013.01); *B01D 2259/4575* (2013.01)

(56) References Cited

U.S. PATENT DOCUMENTS

| | | | | |
|---|---|---|---|---|
| 6,805,732 | B1 | 10/2004 | Billiote et al. | |
| 7,763,206 | B2 | 7/2010 | Mole | |
| 2005/0074359 | A1* | 4/2005 | Krieger | A61L 2/208 |
| | | | | 422/292 |
| 2007/0140932 | A1* | 6/2007 | Bergeron | B03C 3/64 |
| | | | | 422/186.04 |
| 2015/0297771 | A1* | 10/2015 | Law | B01D 53/885 |
| | | | | 423/210 |

OTHER PUBLICATIONS

Aerotec. "Aerotec SANY AIR Komplettpaket" Mar. 25, 2020 (Mar. 25, 2020). pp. 1-8. Retrieved from the Internet: https://cdn.hornbach.de/data/shop/D04/001/780/491/779/644/10292990_Doc_Ol_DE_20200418214654.pdf [retrieved on Aug. 20, 2021](Submission Pending).

Anonymous. "Sprühdose—Wikipedia" Sep. 18, 2017 (Sep. 18, 2017). pp. 1-6. Retrieved from the Internet: https://de.wikipedia.org/w/index.php?title=Spriihdose&oldid=1 69208283 [retrieved on Aug. 20, 2021](Submission Pending).

Mark Onslow. "The value of compressor washes in aviation" May 24, 2019 (May 24, 2019). pp. 1-4. Retrieved from the Internet: https://www.rochem-fyrewash.com/news/41-the-valueof-compressor-washes-in-aviation/ [retrieved on Aug. 23, 2021](Submission Pending).

International Search Report for PCT/FR2021/000042 dated Sep. 2, 2021, 10 pages with English Translation.

Written Opinion of the ISA for PCT/FR2021/000042 dated Sep. 2, 2021, 20 pages with English Translation.

Anonymous. "Disinfectant Spray—Lavender Scent I Seventh Generation," Feb. 26, 2019 (Feb. 26, 2019), Retrieved from the Internet: https://www.seventhgeneration.com/disinfectant-spray-lavender-vanilla-thyme-scent, 8 pages.

Aerotec. "Aerotec SANY AIR Komplettpaket," Mar. 25, 2020 (Mar. 25, 2020), Retrieved from the Internet: https://cdn.hornbach.de/data/shop/D04/001/780/491/779/644/10292990_Doc_01_DE_20200418214654.pdf, 8 pages.

Anonymous. "spray can—Wikipedia," Sep. 18, 2017 (Sep. 18, 2017), Retrieved from the Internet: https://de.wikipedia.org/w/index.php?title=Spriihdose&oldid=169208283, 6 pages.

Mark Onslow. "The value of compressor washes in aviation," May 24, 2019 (May 24, 2019), Retrieved from the Internet: https://www.rochem-fyrewash.com/news/41-the-valueof-compressor-washes-in-aviation/, 4 pages.

* cited by examiner

METHOD AND DEVICE FOR DISINFECTING AND CLEANING ENCLOSED SPACES IN PARTICULAR, SUCH AS A PASSENGER COMPARTMENT ON A MEANS OF TRANSPORT

CROSS-REFERENCE TO RELATED APPLICATIONS

This application is the U.S. national phase of International Application No. PCT/FR2021/000042 filed Apr. 28, 2021, which designated the U.S. and claims priority to U.S. 63/030,541 filed May 27, 2020, U.S. 63/020,157 filed May 5, 2020, and U.S. 63/016,660 filed Apr. 28, 2020, the entire contents of each of which are hereby incorporated by reference.

BACKGROUND OF THE INVENTION

Field of the Invention

The invention relates to technical solutions making it possible to remedy in the best conditions the contamination of the air and solid surfaces by toxic aerosols, bacteria and viruses, in particular in confined spaces such as a passenger reception area in a means of transport.

Description of the Related Art

The air and solid surfaces inside an airplane cabin can be contaminated with aerosols, microdroplets, bacteria and viruses (e.g. Covid-19). These aerosols, microdroplets, bacteria and viruses can come from several sources:

Aerosols, microdroplets, bacteria and viruses introduced by passengers, crew members and technical maintenance staff;

Aerosols, microdroplets, bacteria and viruses from the outside air surrounding the confined space and introduced by the pressurization and/or ventilation circuit of the airplane cabin with air drawn from the airplane engines and air from the pneumatic compressor of the auxiliary power unit (APU);

Aerosols, microdroplets, bacteria and viruses from the pressurization and ventilation circuit of the airplane cabin or the confined space.

These aerosols, microdroplets, bacteria and viruses can be deposited on the solid surfaces of airplane cabins and can potentially poison or infect passengers and crew members.

Although the air recirculation and treatment system inside the cabin is typically equipped with high-performance HEPA (for high-efficiency particulate air) filters, their efficiency and performance can be reduced by the permanent introduction of aerosols, particles and microparticles into the airplane cabin.

Regarding the Covid-19 virus contamination likely to be introduced by passengers, crew members and technical maintenance staff, several contamination introduction routes have been identified among these:

Release of airborne liquid droplets and aerosols containing Covid-19 virus by passengers, crew members or technical maintenance staff infected with this virus;

Influx of the Covid-19 virus by the "cabin" luggage of passengers, crew members or technical servicing and maintenance staff;

Influx of the Covid-19 virus by the clothing and footwear of passengers, crew members or technical servicing and maintenance staff.

For chemical disinfection of the air and solid surfaces inside the airframe of aircraft, called airplane cabin, the following disinfection techniques are commonly applied:

Wiping contaminated surfaces with disinfectant solutions. This solution is very inexpensive in terms of equipment but extremely costly in terms of time and therefore of staff costs. It is sometimes ineffective because the operator cannot disinfect hard-to-reach surfaces;

Spraying disinfectant solutions with electric spray guns of the paint gun type. This solution is also simple to implement, but the droplets produced are too large and the affected surfaces are only partially disinfected;

Spraying using thermal devices: effective in terms of particle size, but the temperature strongly degrades the disinfectant products and it is not recommended to use these thermal methods in indoor spaces.

These various existing techniques for spraying droplets of disinfectant also have several other drawbacks, such as the fact that effective mixing in the air requires a significant amount of time.

A plurality of the aforementioned drawbacks is encountered in vehicles that transport passengers in general and not only for an aircraft.

SUMMARY OF THE INVENTION

On the basis of these observations, the applicants have carried out research aimed at preventing these contaminations.

This research has led to the design and production of a new method and device making it possible to provide a global solution for disinfecting and/or for preventing contamination of the air and surfaces, in particular of confined spaces such as a passenger cabin of a transport vehicle.

According to the invention, the disinfection and purification method for preventing contamination of a transport vehicle having a passenger reception area equipped with a ventilation circuit, contamination by aerosols, microdroplets, bacteria or viruses, is remarkable in that it includes the following operation steps:

Installation in the ventilation circuit of the reception area of at least one capacitor filter with porous armatures and dielectric, impregnated or not with bactericidal or virucidal substances that are not releasable into the ventilation air circuit of the reception area, which capacitor filter is connected to the positive and negative poles of an electricity generator;

Creation of a swirling vortex of aerosols and microdroplets of a disinfectant liquid or aerosols or microdroplets of a disinfectant liquid by means of a gas, called driving gas;

Bringing the aerosols or microdroplets of disinfectant liquid into contact with the aerosols and microdroplets likely to contain bacteria and viruses by spraying the created swirling mixture on the clothing and luggage of the passengers before they enter the reception area, Bringing the aerosols or microdroplets of disinfectant liquid into contact with the aerosols and microdroplets likely to contain bacteria and viruses by spraying the created mixture on the solid surfaces and/or in the air of the reception area to be disinfected.

The term "passengers" used herein includes both persons being transported and flight and technical staff having access to the reception area.

This method is remarkable in that it offers a global solution by providing filtration and disinfection.

Filtration, by a capacitor filter with porous armatures and dielectric, which capacitor filter is connected to the positive and negative poles of an electricity generator, of the air circulating in the reception area, and disinfection of the various surfaces with which the air or the passengers are likely to come into contact, as well as the clothing or luggage of the passengers, the crew members and technical staff likely to enter the area.

It can also be associated with individual passenger protection means.

The step of filtration by capacitor filter with porous armatures and dielectric, which capacitor filter is connected to the positive and negative poles of an electricity generator, is greater than that of the HEPA filters hitherto used.

The step of creating a vortex makes it possible to create a swirling mixture and significant friction (energetic contact) between the particles and/or microdroplets of a disinfectant liquid and:

Aerosols, particles and microparticles containing bacteria or viruses, suspended in the air, Aerosols, particles and microparticles containing bacteria or viruses and deposited on solid surfaces.

The mixture created by the swirling vortex is indeed turbulent.

The prior art does not provide swirling mixture and significant friction between the particles, microparticles and aerosols (solid and liquid) suspended in the air and containing bacteria or viruses and the microparticles and aerosols of the disinfectant, which prevents the spread of the disinfectant within the aerosols, particles and microparticles containing bacteria or viruses.

According to another particularly advantageous feature of the invention, the aerosols and/or microdroplets of disinfectant liquid are created by annular suction of a disinfectant liquid by the flowing driving gas.

According to a particularly advantageous feature of the invention, the driving gas is selected from the following list:

pressurized air or pressurized nitrogen or pressurized oxygen or pressurized CO2, or a mixture of air and CO2 under pressure, or a mixture of oxygen and CO2 under pressure, or a mixture of nitrogen and CO2 under pressure.

According to another feature of the invention, the pressure of the driving gas is set to be between 1 and 300 bars.

This driving gas can be produced from a compressed gas network (e.g. compressed air) or from a pressurized gas cylinder (air cylinder or oxygen cylinder) or from a gas compressor (e.g. electric air compressor).

According to another particularly advantageous feature of the invention, the disinfectant liquid is composed of at least one of the elements from the following list:

hydrogen peroxide or peracetic acid, a chlorine dioxide-based compound, a quaternary ammoniums-based compound, an alcoholic compound, potassium monopersulfate or potassium persulfate or persulfate, a mixture of several disinfectants, any approved disinfectant.

According to another particularly advantageous feature of the invention, the method comprises the step of heating the mixture to be sprayed, which improves its properties.

According to another particularly advantageous feature of the invention, the disinfectant liquid is subjected to bubbling by a part of the driving gas and the bubbled mixture is then sucked up by the annular flow of the driving gas.

Such a method makes it possible to filter and disinfect the air and the surfaces, in particular of a confined space such as a passenger reception area in a passenger transport vehicle.

It also makes it possible, in the context of an application to an aircraft, to eliminate particles, microparticles and aerosols containing bacteria or viruses deposited on the internal walls and the blades of the compressors of aircraft engines, on the one hand and:

a. aerosols, particles and microparticles (toxic) present in the pressurization system of the aircraft cabin and resulting from the leakage of liquid lubricants from airplane engines, b. aerosols, particles and microparticles containing bacteria or viruses (e.g. Covid-19) present in the pressurization system of the airplane cabin and resulting from air pollution in epidemic and pandemic areas, which polluted air is itself derived from the surrounding air sucked in and compressed by the aircraft engines, on the other hand.

Thus, according to another particularly advantageous feature of the invention where the means of transport is an aircraft equipped with an engine and a compressor, the disinfection method comprises a step of spraying the created mixture on the aircraft engine and on its compressor, for washing purposes.

This step may complement those already mentioned.

According to a preferred but non-limiting embodiment, the mixture contains in this case hot water at a temperature of between 60 and 90° C. and containing a disinfectant that is not corrosive for the engine.

These filters can also be used to eliminate contaminated aerosols, particles and microparticles present in the pneumatic pressurization system of the auxiliary electricity generator (APU) of the aircraft prior to their introduction into the aircraft cabin or airframe.

As explained above, it is also planned to supplement these technical disinfection solutions with the measures described below.

It is possible to reduce the risks of introducing contamination inside the passenger reception area (such as the cabin of an airplane) by passengers, crew members and servicing and maintenance technical staff by the following operations:

Testing passengers, crew members and technical maintenance staff before they enter the airplane cabin (in order to detect Covid-19 virus-infected persons). For this purpose, autonomous terminals for the automatic detection of viruses and bacteria contained in the aerosols and microdroplets emitted by any infected person may be used;

Disinfecting (through the installation of disinfection gates) the luggage of passengers and the crew members or the maintenance and servicing technical staff before their loading or introduction into the airplane;

Disinfecting (through the installation of disinfection gates) the clothing and footwear of passengers, crew members and technical service and maintenance staff before they enter the airplane;

Carry out a point-to-point tracing of people who are ill with COVID-19 and intending to fly. For this purpose, the method of detection and tracing can be used.

Furthermore, it is also possible to reduce the risks of contamination by equipping the persons being transported with individual protection means.

Another object of the invention is the device making it possible to filter by means of a capacitor filter on the one hand and to create the disinfecting swirling vortex on the other hand, in order to implement the method described above.

According to a particularly advantageous feature of the invention, the device is remarkable in that the capacitor filter with porous armatures and dielectric, which capacitor filter is connected to the positive and negative poles of an electricity generator, comprises an inlet for the gaseous fluid to be filtered and an outlet for the filtered gaseous fluid, said gaseous fluid to be filtered passing through a succession of layers of different porous materials according to at least the following scheme:

At least one layer of non-conductive material sandwiched between two layers of conductive material.

The implementation of the method may include one or more capacitor filters which can be connected in series or in parallel.

In addition, this or these capacitor filters may or may not be associated with one or more electropositive filters.

According to another particularly advantageous feature of the invention, the conductive porous material layer comprises at least one of the materials from the following list:

titanium, titanium alloy, stainless steel, nickel, nickel alloy, silver, gold, graphite, carbon, carbon fiber, hastelloy, platinum, graphene.

According to another particularly advantageous feature of the invention, the non-conductive porous material layer comprises at least one of the materials from the following list:

Polyethylene, Polypropylene, PTFE, Polyamide, Polyether sulfone.

According to another particularly advantageous feature of the invention, a HEPA filter forms the non-conductive porous material layer.

The conductive materials are associated with a DC voltage generator with one or more electrical capacitors.

The capacitor filter can be mounted in series or in parallel with the said one or more electrical capacitors.

The voltage supplied by the generator has a value between 0.1 and 1000 volts.

The one or more capacitors are polarized or non-polarized and their electrical capacitance is between 0.1 and 500,000 microfarads.

According to another particularly advantageous feature of the invention, the capacitor filter with porous armatures and dielectric, which capacitor filter is connected to the positive and negative poles of an electricity generator, also contains activated carbon and/or a catalyst for neutralizing atmospheric ozone.

By adjusting the succession and the selection of the materials passed through, their thickness and their electricity supply (for the conductive material layers), the filtration obtained is very efficient and superior to that proposed by the prior art.

According to another particularly advantageous feature of the invention, the device is equipped with a nozzle creating the swirling vortex in its hollow core part, said nozzle comprising two ends, with at a first end, an inlet orifice for the so-called driving gas, and at the second end, the outlet in the form of a swirling vortex of the mixture, said nozzle comprising an orifice that communicates with a volume of disinfectant liquid, which orifice emerges into the hollow core part by means of a channel arranged coaxially with the axis of the flow of driving gas and at the center thereof, so that the driving gas creates an annular flow around the central flow of disinfectant liquid so that the disinfectant liquid is sucked by the displacement of said driving gas in the hollow core part and that the mixture is swirled and turbulent.

According to another particularly advantageous feature of the invention, the orifice communicating with the volume of disinfectant liquid allows bubbling by the driving gas.

According to another particularly advantageous feature, the hollow core part is preformed so as to direct the flows and cause them to swirl.

The fundamental concepts of the invention having been set forth above in their most elementary form, other details and features will emerge more clearly upon reading the following description and with reference to the appended drawings, which show, by way of non-limiting examples, embodiments of a method and of a device in accordance with the invention.

DESCRIPTION OF THE PREFERRED EMBODIMENTS

Figure 1:
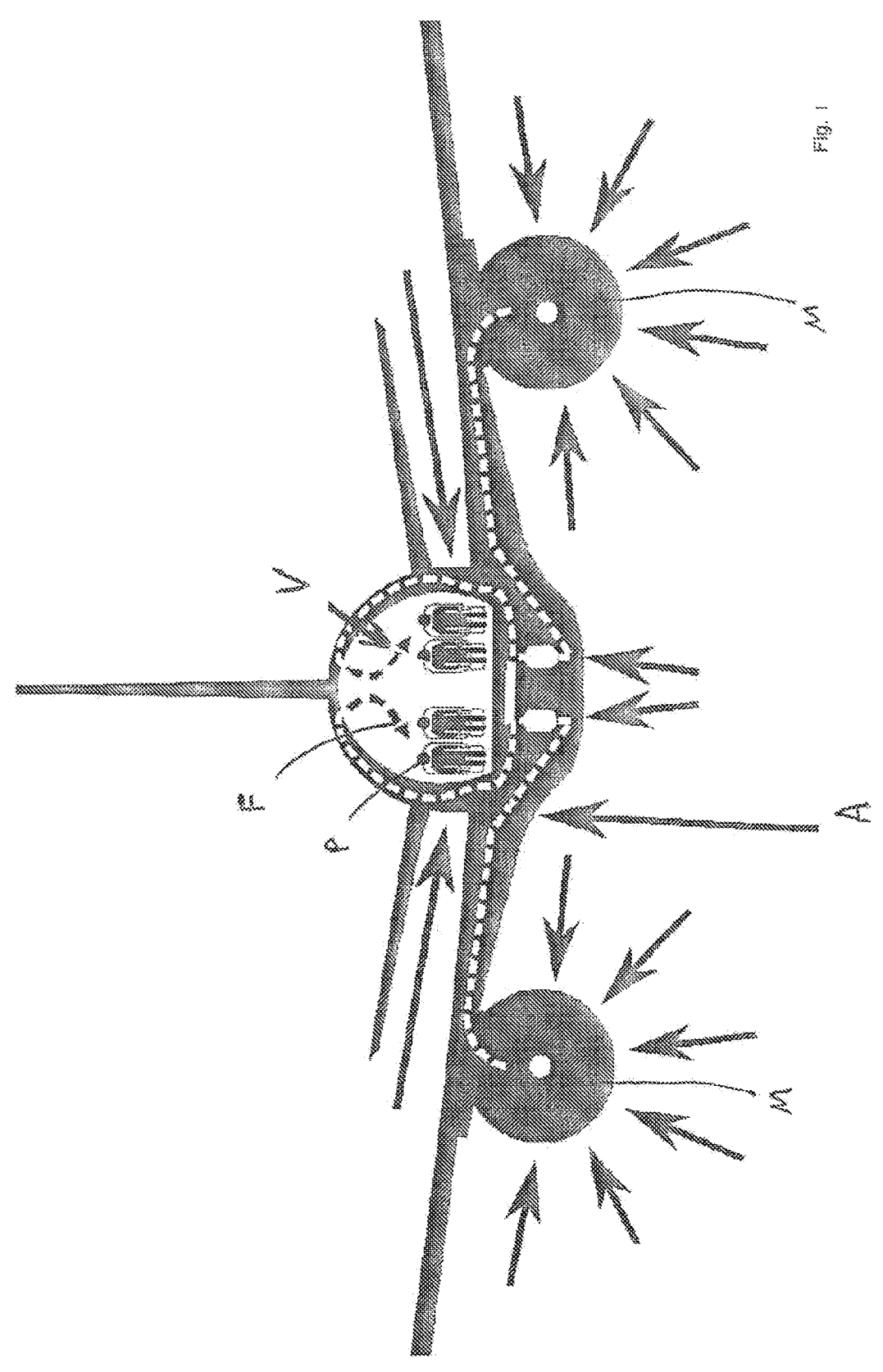
FIG. 1 is a schematic drawing of an aircraft showing the various possibilities of contamination.

As illustrated in FIG. 1, the airframe of the aircraft, here an airplane denoted A as a whole, can be contaminated in different ways.

Thus, in addition to the contamination likely to originate from the passengers P, crew members or technical staff, the atmosphere in which the airplane A is operating, but also the technical sub-assemblies through which the air intended for the reception area V accommodating the passengers P it is likely to pass, can also be the source of contamination.

As explained above, the aerosols, particles and microparticles resulting from the leakage of liquid lubricants from the engines M of airplane A, aerosols, particles and microparticles containing bacteria and/or viruses (e.g. COVID 19) resulting from pollution, cause the flow F of air circulating in the area to be susceptible to be contaminated.

To avoid this, the applicants propose a global method making it possible to filter the air before it enters the reception area by means of a capacitor filter and to disinfect the various surfaces with which the air is likely to come into contact by spraying a vortex containing particles of disinfectant.

Figure 2:
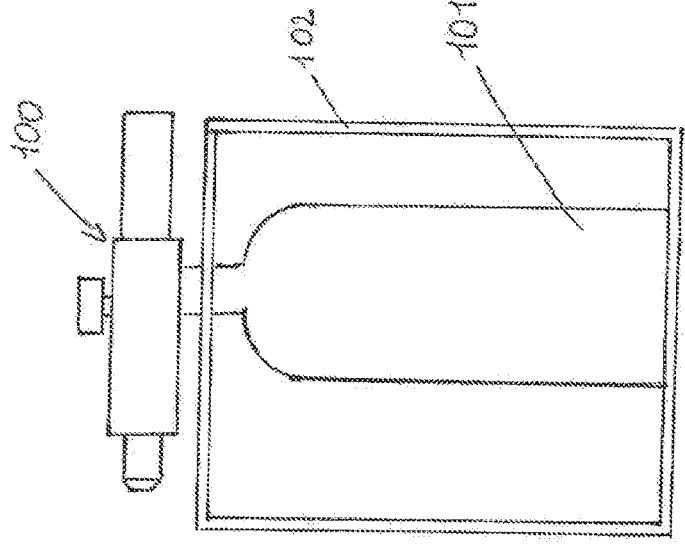
FIG. 2 is a schematic drawing of an embodiment in accordance with the invention of a device for creating a swirling vortex.

As illustrated by FIG. 2, the functional sub-assembly 100 for creating said vortex includes a nozzle 100 and a tank 101 of liquid disinfectant disposed in a housing 102, the nozzle 100 being attached to the outer surface of the housing 102. By the action of a driving gas, the nozzle 100 creates a vortex which sucks up the disinfectant and creates a swirling and turbulent mixture containing the particles of disinfectant.

Figure 3:
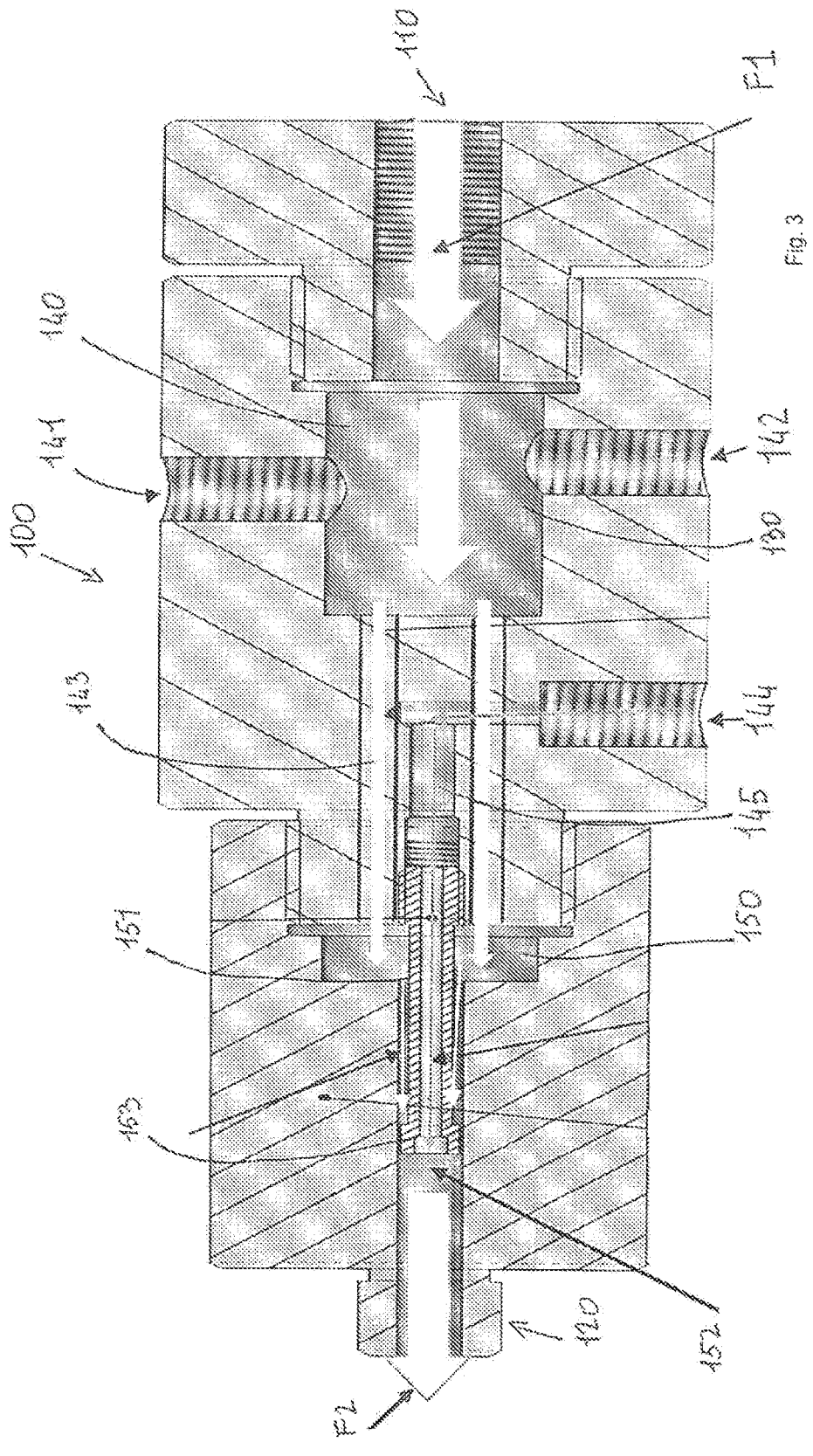
FIG. 3 is a schematic drawing of a sectional view of one embodiment of a nozzle.

To this end, as illustrated by FIG. 3, the nozzle 100 comprises two ends, with at a first end 110, an inlet orifice for the so-called driving gas F1, and at the second end 120, an outlet orifice of a swirling vortex of a mixture combining driving gas and particles of a disinfectant.

The nozzle is preformed with a hollow core part 130 having, starting from the inlet of the driving gas F1, a succession of volumes having various functions.

Thus, the driving gas F1 emerges into a first chamber 140 with which two ducts communicate:

A first transverse duct 141 communicating with an external orifice making it possible to install a pressure control monometer in the first chamber 140;

A second transverse duct 142 communicating with another external orifice allowing the entry of another driving gas or the exit of a part of the driving gas F1 for the bubbling of the disinfectant liquid.

This first chamber 143 emerges into a second chamber 150 by means of longitudinal ducts 143 arranged around the axis of the nozzle 100.

The same part of the nozzle 100 accommodating the chamber 140 is preformed with a transverse duct 144 communicating with an external orifice allowing the entry of disinfectant liquid stored in the tank 101 (see FIG. 2).

The hollow core part 130 is furthermore preformed with an axial duct 145 arranged in such a way that the longitudinal ducts are arranged around it and with which said transverse duct 144 communicates. This axial duct 145 is extended by a tube 151 passing through the second chamber 150. Thus, the disinfectant liquid does not emerge into the second chamber 150.

This second chamber 150 emerges into an axial bore 152 with a diameter greater than the external diameter of the tube 151 in such a way as to create a clearance allowing an annular flow of the driving gas from the chamber 150 around the tube 151. This tube 151 emerges into said bore so that its outlet orifice is subjected to said annular flow which therefore creates a depression causing a suction to which the disinfectant liquid is subjected. The vortex thus creates mixing in the bore 152 between the driving gas and the disinfectant liquid downstream of the outlet orifice of the tube 151 and just before the outlet orifice of the second end 120. The outlet flow F2 is driven by said vortex and is therefore swirling and turbulent.

As illustrated, the tube 151 is screwed into the preformed body of the duct 145 and coaxially with the latter so that its position can be adjusted. Indeed, the outlet end 153 of said tube 151 is equipped with a peripheral flange creating a constriction for the annular flow of driving gas, the position of which constriction can be adjusted thanks to the helical connection.

According to a non-limiting embodiment, this flange is preformed with blades directing the flow of driving gas so as to create a swirl.

Several filter embodiments are possible for implementing filtration by a capacitor filter according to the invention, but they all adopt a basic configuration described below.

The filter comprises an inlet for the gaseous fluid to be filtered and an outlet for the filtered gaseous fluid, said gaseous fluid to be filtered passing through a succession of layers of different porous materials according to the following scheme:

At least one layer of non-conductive material sandwiched between two layers of conductive material.

The conductive porous material is from the following list:

titanium, titanium alloy, stainless steel, nickel, nickel alloy, silver, gold, graphite, carbon, carbon fiber, hastelloy, platinum, graphene.

The non-conductive porous material is from the following list:

Polyethylene, Polypropylene, PTFE, Polyamide, Polyether sulfone, HEPA filter.

Figure 4:
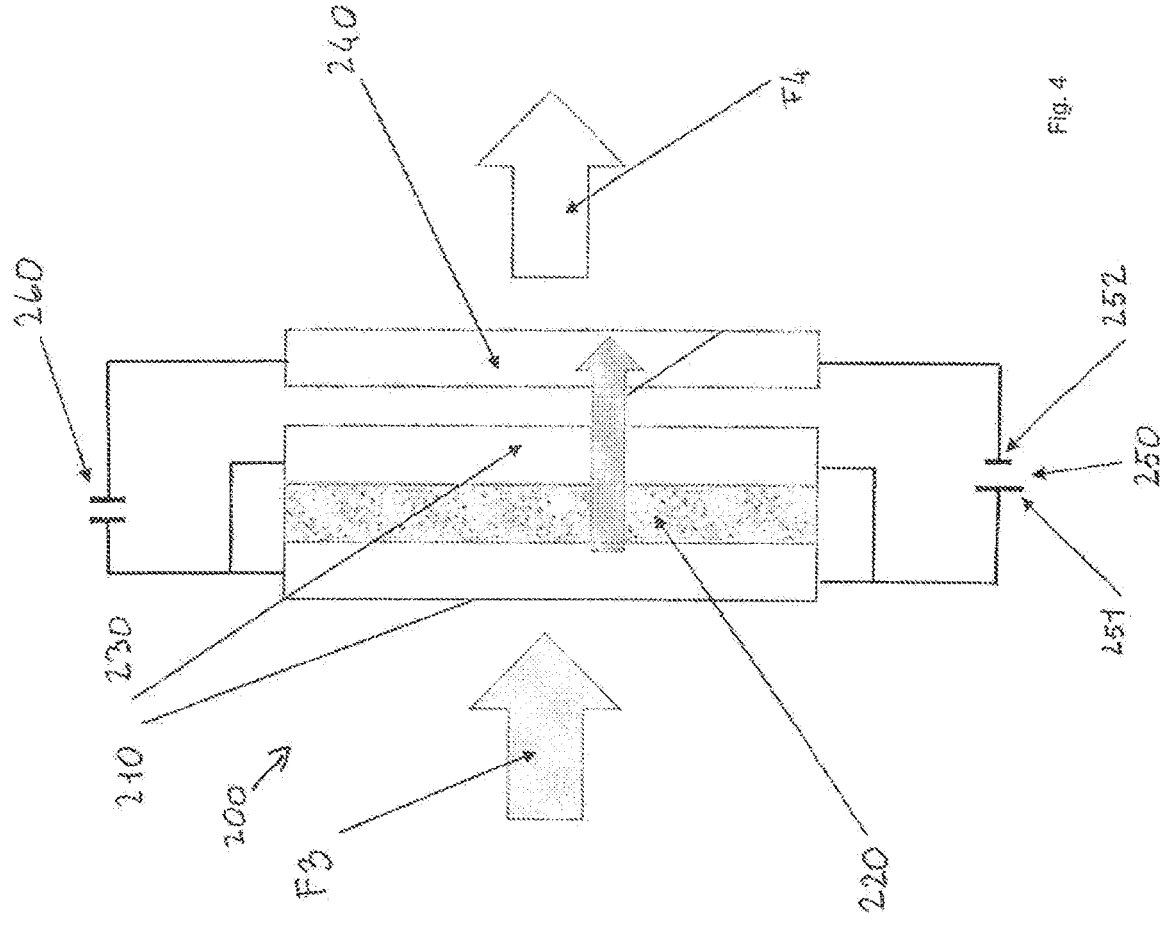
FIG. 4, FIG. 5, FIG. 6, FIG. 7, FIG. 8 and FIG. 9 are schematic drawings of embodiments in accordance with the invention of a capacitor filter.

Among these, the filter 200 illustrated in FIG. 4 comprises three associated layers 210, 220, 230 and a dissociated fourth layer 240. The three associated layers are arranged to sandwich a non-conductive porous material layer 220 by the layers of conductive porous material 210 and 230. The layer 240 is a conductive porous material layer.

A DC voltage generator 250 provides power to the conductive layers. The positive pole 251 is connected to the layers 210 and 230 of the associated layers and the negative pole 252 is connected to the dissociated layer 240.

A capacitor 260 is also connected to the conductive layers, one electrode being connected to layers 210 and 230 of the associated layers and the other electrode being connected to the dissociated layer.

The potentially contaminated air flow F3 passes through these layers and a filtered air flow F4 exits therefrom.

Figure 5:
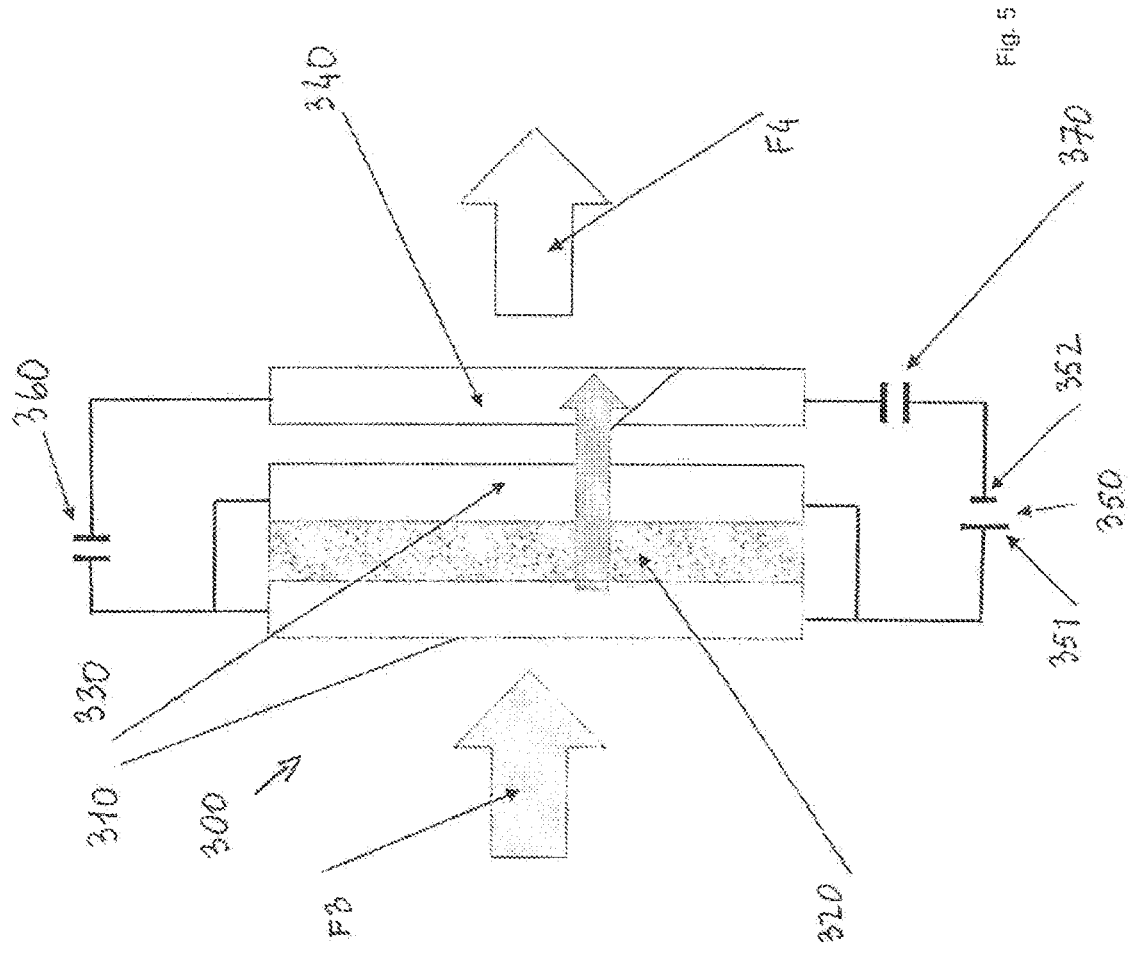

The filter 300 illustrated in FIG. 5 comprises three associated layers 310, 320, 330 and a dissociated fourth layer 340. The three associated layers are arranged to sandwich a non-conductive porous material layer 320 by the layers of conductive porous material 310 and 330. The layer 340 is a conductive porous material layer.

A DC voltage generator 350 provides power to the conductive layers. The positive pole 351 is connected to the layers 310 and 330 of the associated layers and the negative pole 352 is connected to the dissociated layer 340.

A capacitor 360 is also connected to the conductive layers, one electrode being connected to layers 310 and 330 of the associated layers and the other electrode being connected to the dissociated layer 340.

Another capacitor 370 is interposed between the negative pole 352 and the dissociated layer 340.

Figure 6:
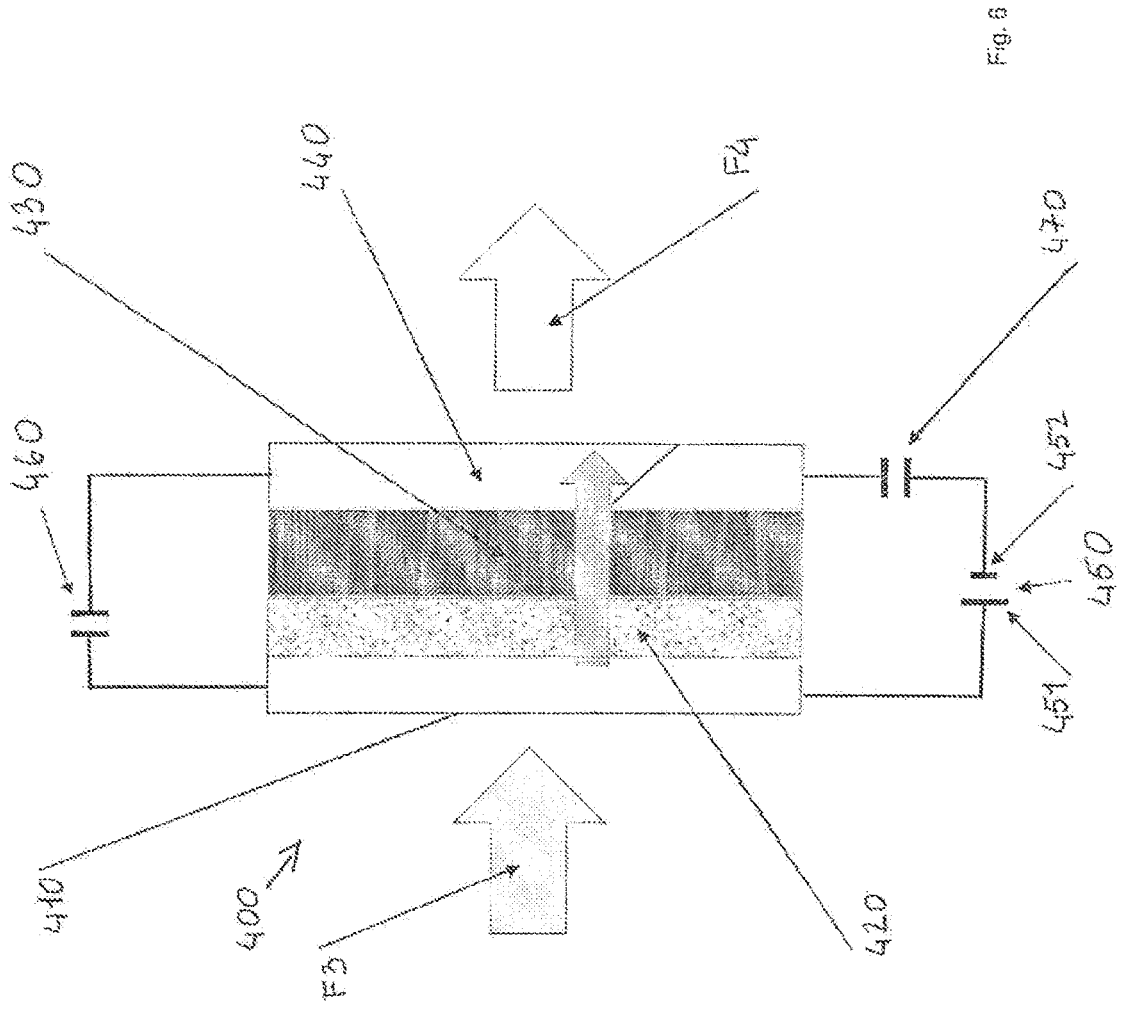

The filter 400 illustrated by FIG. 6 includes four associated layers 410, 420, 430 and 440. Layers 410 and 440 are made of conductive porous material. Layer 420 is made of non-conductive porous material. Layer 430 is made of porous material and is made of at least one of the materials in the following list:

activated carbon, activated carbon fiber, graphene.

The four associated layers are arranged so as to sandwich the non-conductive porous material layer 420 and the layer 430 by the layers of conductive porous material 410 and 440. The fluid to be filtered first passes through the non-conductive porous material 420 then through the layer 430.

A DC voltage generator 450 provides power to the conductive layers 410 and 440. The positive pole 451 is connected to the layer 410 and the negative pole 452 is connected to the layer 440.

A capacitor 460 is also connected to the conductive layers, one electrode being connected to layer 410 and the other electrode being connected to layer 440.

Another capacitor 470 is interposed between the negative pole 452 and the layer 440.

Figure 7:
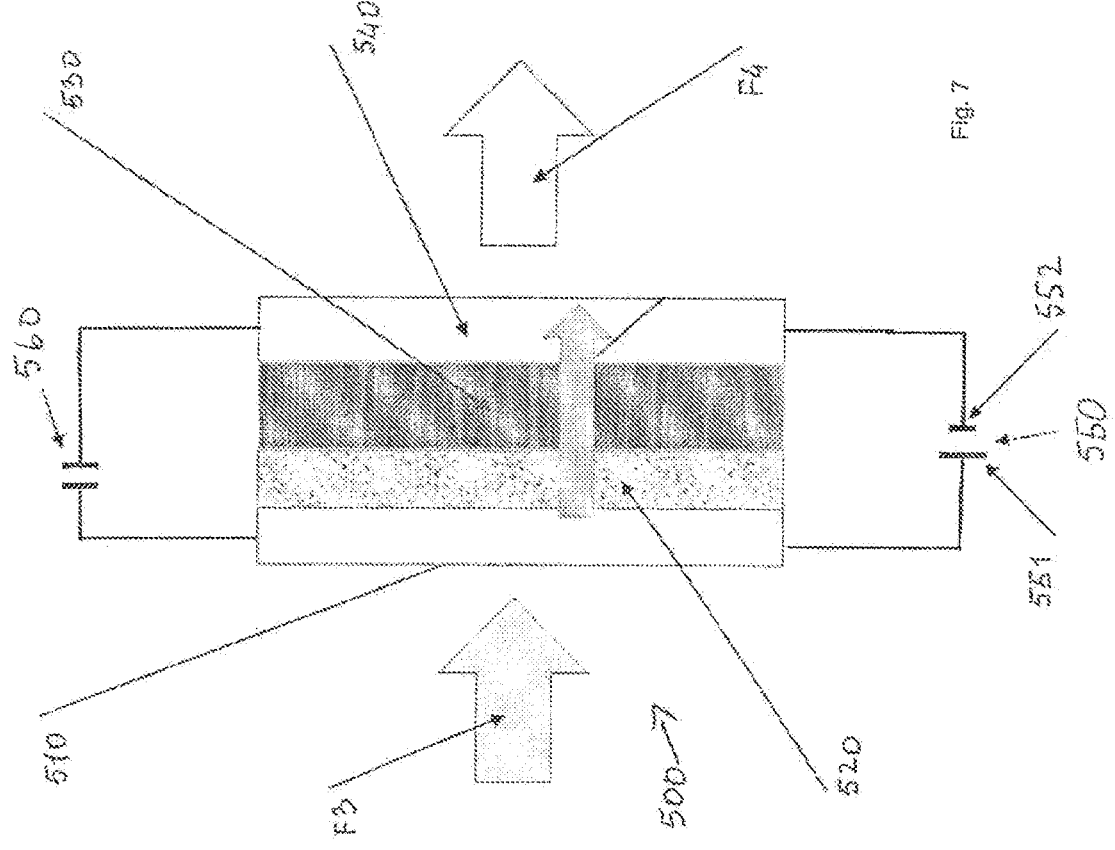

The filter 500 illustrated by FIG. 7 includes four associated layers 510, 520, 530 and 540. The layers 510 and 540 are made of conductive porous material. Layer 520 is made of non-conductive porous material. Layer 530 is made of porous material and is made of at least one of the materials in the following list:

activated carbon, activated carbon fiber, graphene.

The four associated layers are arranged so as to sandwich the non-conductive porous material layer 520 and the layer 530 by the layers of conductive porous material 510 and 540. The fluid to be filtered first passes through the non-conductive porous material then through the layer 530.

A DC voltage generator 550 provides power to the conductive layers 510 and 540. The positive pole 551 is connected to the layer 510 and the negative pole 552 is connected to the layer 540.

A capacitor 560 is also connected to the conductive layers, one electrode being connected to the layer 510 and the other electrode being connected to the layer 540.

Figure 8:
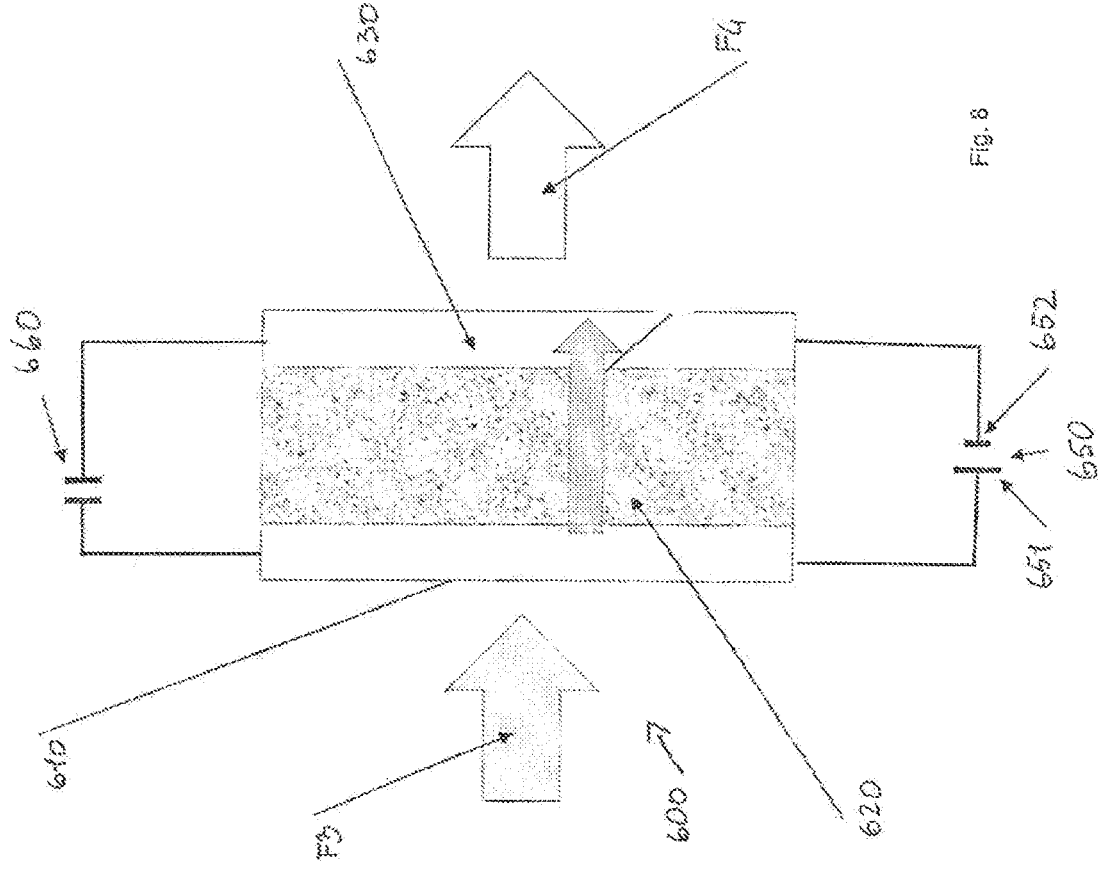

The filter 600 illustrated by FIG. 8 comprises three associated layers 610, 620, 630. The three associated layers are arranged so as to sandwich a non-conductive porous material layer 620 of great thickness by the layers of conductive porous material 610 and 630.

A DC voltage generator 650 provides power to the conductive layers. The positive pole 651 is connected to the layer 610 and the negative pole 652 is connected to the layer 630.

A capacitor 660 is also connected to the conductive layers, one electrode being connected to layer 610 and the other electrode being connected to dissociated layer 630.

Figure 9:
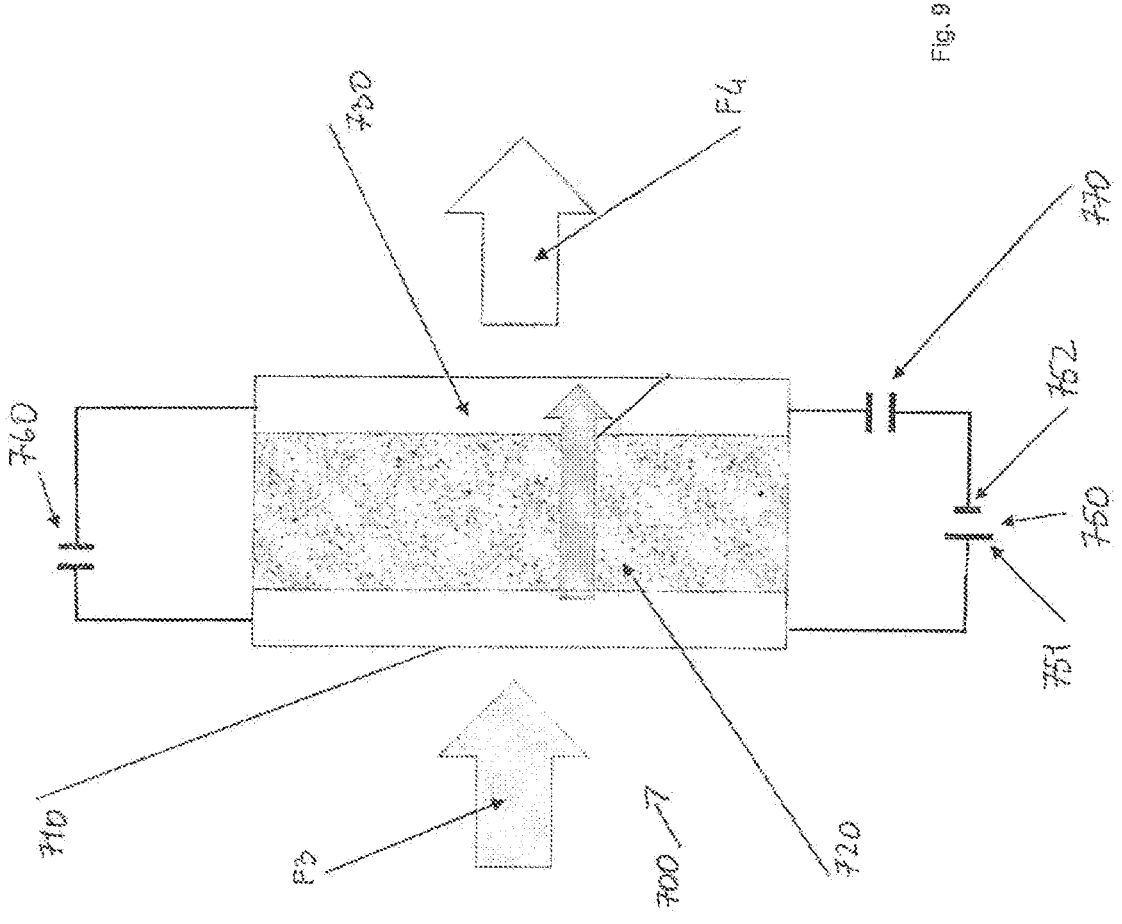

The filter 700 illustrated by FIG. 9 comprises three associated layers 710, 720, 730. The three associated layers are arranged so as to sandwich a non-conductive porous material layer 720 of great thickness by the layers of conductive porous material 710 and 730.

A DC voltage generator 750 provides power to the conductive layers. The positive pole 751 is connected to the layer 710 and the negative pole 752 is connected to the layer 730.

A capacitor 760 is also connected to the conductive layers, one electrode being connected to the layer 710 and the other electrode being connected to the dissociated layer 730.

Another capacitor 770 is interposed between the negative pole 752 and the layer 730.

It is understood that the devices which have been described hereinabove and depicted have been described for the purpose of disclosure rather than limitation. Of course, various arrangements, modifications and improvements may be made to the above examples, without departing from the scope of the invention.

Thus, for example, it is understood that the features described above for an application to an aircraft are likely to apply to any passenger transport vehicle.

The invention claimed is:

1. A method for disinfecting and purifying to prevent contamination of transport vehicle including an engine, a compressor, and a passenger reception area equipped with a ventilation air circuit, contamination by aerosols, microdroplets, bacteria or viruses, the method comprising:

installing, in the ventilation circuit of the passenger reception area, at least one capacitor filter with porous armatures and dielectric, impregnated or not with bactericidal or virucidal substances that cannot be released into the ventilation air circuit of the passenger reception area, the at least one capacitor filter being connected to the positive and negative poles of an electricity generator;

creating a swirling vortex of aerosols and microdroplets of a disinfectant liquid or aerosols or microdroplets of a disinfectant liquid by a driving gas;

bringing the aerosols or the microdroplets of disinfectant liquid into contact with aerosols and microdroplets likely to contain bacteria and viruses by spraying the created swirling vortex mixture on clothing and luggage of passengers before the passengers enter the passenger reception area;

bringing the aerosols or microdroplets of disinfectant liquid into contact with the aerosols and microdroplets likely to contain bacteria and viruses by spraying the created swirling vortex mixture one or more of: (i) on solid surfaces and (ii) in the air of the passenger reception area to be disinfected; and spraying the created mixture on the engine of the aircraft and on the compressor to wash the aircraft.

2. The method according to claim 1, wherein one or more of the aerosols and the microdroplets of disinfectant liquid are created by annular suction of the disinfectant liquid by the flowing driving gas.

3. The method according to claim 2, wherein the driving gas is selected from one of:

pressurized air or pressurized nitrogen or pressurized oxygen or pressurized $CO_2$, a mixture of air and $CO_2$ under pressure, a mixture of oxygen and $CO_2$ under pressure, and a mixture of nitrogen and $CO_2$ under pressure.

4. The method according to claim 2, wherein the pressure of the driving gas is set to be between 1 and 300 bars.

5. The method according to claim 2, wherein the disinfectant liquid is composed of at least one of:

hydrogen peroxide or peracetic acid, a chlorine dioxide-based compound, a quaternary ammoniums-based compound, an alcoholic compound, potassium monopersulfate or potassium persulfate or persulfate, and a mixture of several disinfectants.

6. The method according to claim 1, wherein the driving gas is selected from one of:

pressurized air or pressurized nitrogen or pressurized oxygen or pressurized $CO_2$, a mixture of air and $CO_2$ under pressure, a mixture of oxygen and $CO_2$ under pressure, and a mixture of nitrogen and $CO_2$ under pressure.

7. The method according to claim 6, wherein the pressure of the driving gas is set to be between 1 and 300 bars.

8. The method according to claim 6, wherein the disinfectant liquid is composed of at least one of:

hydrogen peroxide or peracetic acid, a chlorine dioxide-based compound, a quaternary ammoniums-based compound, an alcoholic compound, potassium monopersulfate or potassium persulfate or persulfate, and a mixture of several disinfectants.

9. The method according to claim 1, wherein the pressure of the driving gas is set to be between 1 and 300 bars.

10. The method according to claim 1, wherein the disinfectant liquid is composed of at least one of:

hydrogen peroxide or peracetic acid, a chlorine dioxide-based compound, a quaternary ammoniums-based compound, an alcoholic compound, potassium monopersulfate or potassium persulfate or persulfate, and a mixture of several disinfectants.

US 12,599,691 B2

11

11. The method according to claim 1, further comprising heating the mixture to be sprayed.

12. The method according to claim 1, wherein the disinfectant liquid is subjected to bubbling by a part of the driving gas and the bubbled mixture is then sucked up by the annular flow of the driving gas.

\* \* \* \* \*

12